United States Patent
An

(10) Patent No.: US 12,168,082 B2
(45) Date of Patent: Dec. 17, 2024

(54) COMPOSITION FOR REGENERATION OF HUMAN FIBROUS CARTILAGE OR ELASTIC CARTILAGE

(71) Applicant: Medicrinia, Co., Ltd., Seoul (KR)

(72) Inventor: Seung Uk An, Paju-si (KR)

(73) Assignee: Medicrinia, Co., Ltd., Seoul (KR)

( * ) Notice: Subject to any disclaimer, the term of this patent is extended or adjusted under 35 U.S.C. 154(b) by 613 days.

(21) Appl. No.: 16/958,843

(22) PCT Filed: Dec. 28, 2018

(86) PCT No.: PCT/KR2018/016892
§ 371 (c)(1),
(2) Date: Jun. 29, 2020

(87) PCT Pub. No.: WO2019/132604
PCT Pub. Date: Jul. 4, 2019

(65) Prior Publication Data
US 2021/0069376 A1  Mar. 11, 2021

(30) Foreign Application Priority Data
Dec. 29, 2017  (KR) .................. 10-2017-0183688

(51) Int. Cl.
*A61L 27/22* (2006.01)
*A61L 27/18* (2006.01)
*A61L 27/36* (2006.01)
*A61L 27/52* (2006.01)
*A61L 27/54* (2006.01)
*C08L 71/02* (2006.01)

(52) U.S. Cl.
CPC ............. *A61L 27/225* (2013.01); *A61L 27/18* (2013.01); *A61L 27/3616* (2013.01); *A61L 27/3654* (2013.01); *A61L 27/3687* (2013.01); *A61L 27/52* (2013.01); *A61L 27/54* (2013.01); *C08L 71/02* (2013.01); *A61L 2300/254* (2013.01); *A61L 2430/06* (2013.01)

(58) Field of Classification Search
None
See application file for complete search history.

(56) References Cited

U.S. PATENT DOCUMENTS

2015/0166735 A1* 6/2015 Bidault ................. A61L 29/041
424/487
2015/0320833 A1  11/2015 Stice et al.

FOREIGN PATENT DOCUMENTS

| AU | 7595698 | * | 12/1998 |
| CN | 105979976 | * | 9/2019 |
| KR | 20120046430 A | | 5/2012 |
| KR | 20170116811 A | | 10/2017 |
| WO | 2016112176 A1 | | 7/2016 |

OTHER PUBLICATIONS

"International Preliminary Report on Patentability corresponding to International Application No. PCT/KR2018/016892 mailed Jul. 9, 2020".
"International Search Report and Written Opinion corresponding to International Application No. PCT/KR2018/016892 mailed May 31, 2019".
Gsib, Olfat L, et al., "Evaluation of Fibrin-Based Interpenetrating Polymer Networks as Potential Biomaterials for Tissue Engineering", Nanomaterials 7(12):3, 11 (Dec. 10, 2017) 21 pages.
Vega, S.R L, et al., "Recent Advances in Hydrogels for Cartilage Tissue Engineering", Eur. Cell Mater. 33:59-75 (2017).

* cited by examiner

*Primary Examiner* — Melissa S Mercier
(74) *Attorney, Agent, or Firm* — Myers Bigel, P.A.

(57) ABSTRACT

The present invention relates to a composition and a kit for regeneration and treatment of cartilage, preferably, fibrous cartilage or elastic cartilage and a regeneration method using the same. A composition and a kit for cartilage regeneration according to the present invention may be administered simply in a minimally invasive manner to a site in which fibrous cartilage or elastic cartilage is needed to be regenerated or restored from injury, exhibit resistance to degradation enzymes without toxicity within the body, and are attached to or detained at and thus retained at the injured, administered site, whereby behavioral improvement may be brought about in surrounding cells, which leads to effectively inducing defected tissues of the meniscus to be regenerated. Therefore, the composition of the present invention is useful as a mediator for aiding the regeneration of biological tissue defected regions in the biomaterials field.

6 Claims, 8 Drawing Sheets

<FIG 1>
A
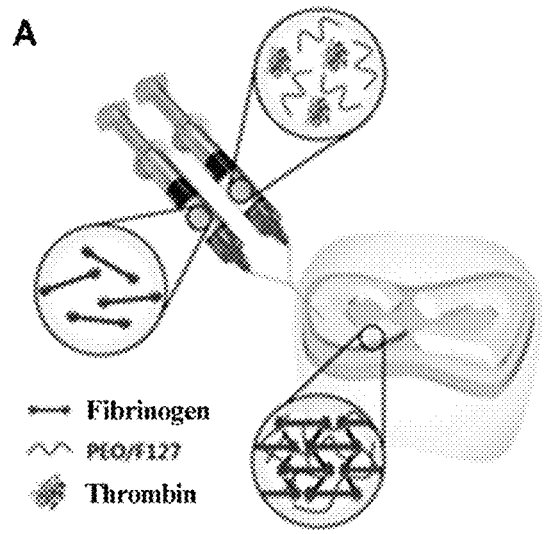
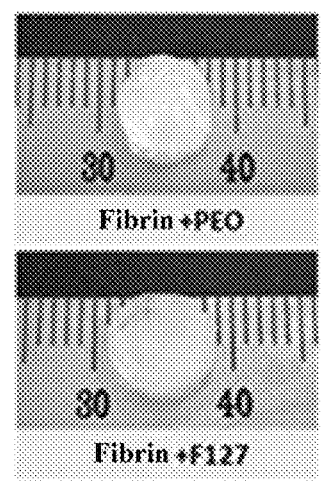
— Fibrinogen
〜 PEO/F127
● Thrombin
B
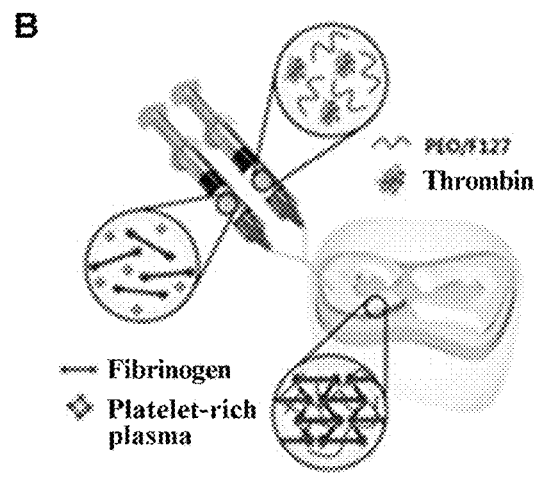
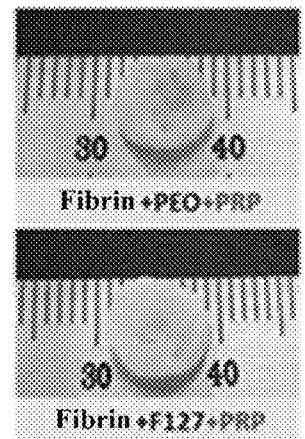
〜 PEO/F127
● Thrombin
— Fibrinogen
◇ Platelet-rich plasma <FIG 2>
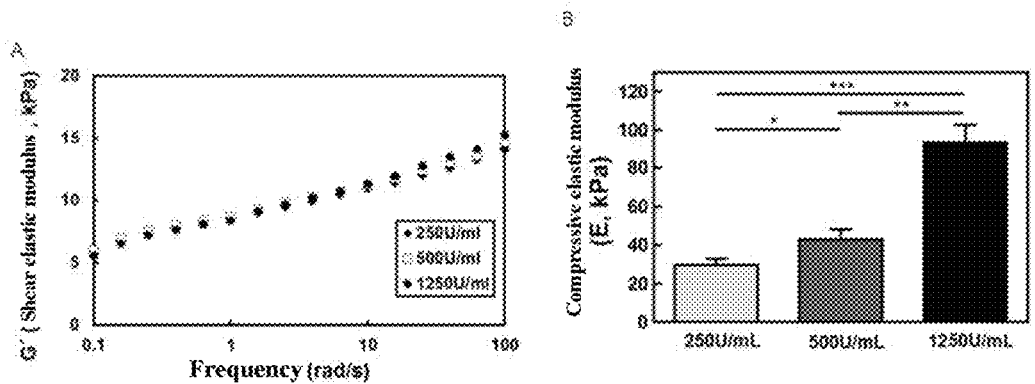
<FIG 3>
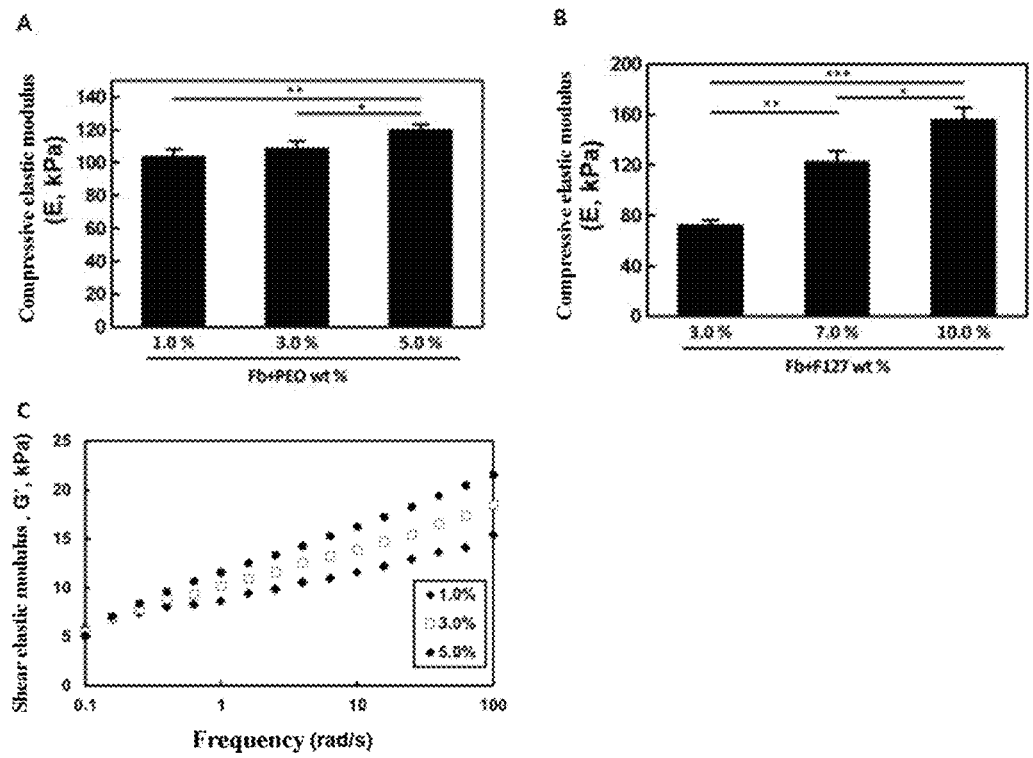

<FIG 4>
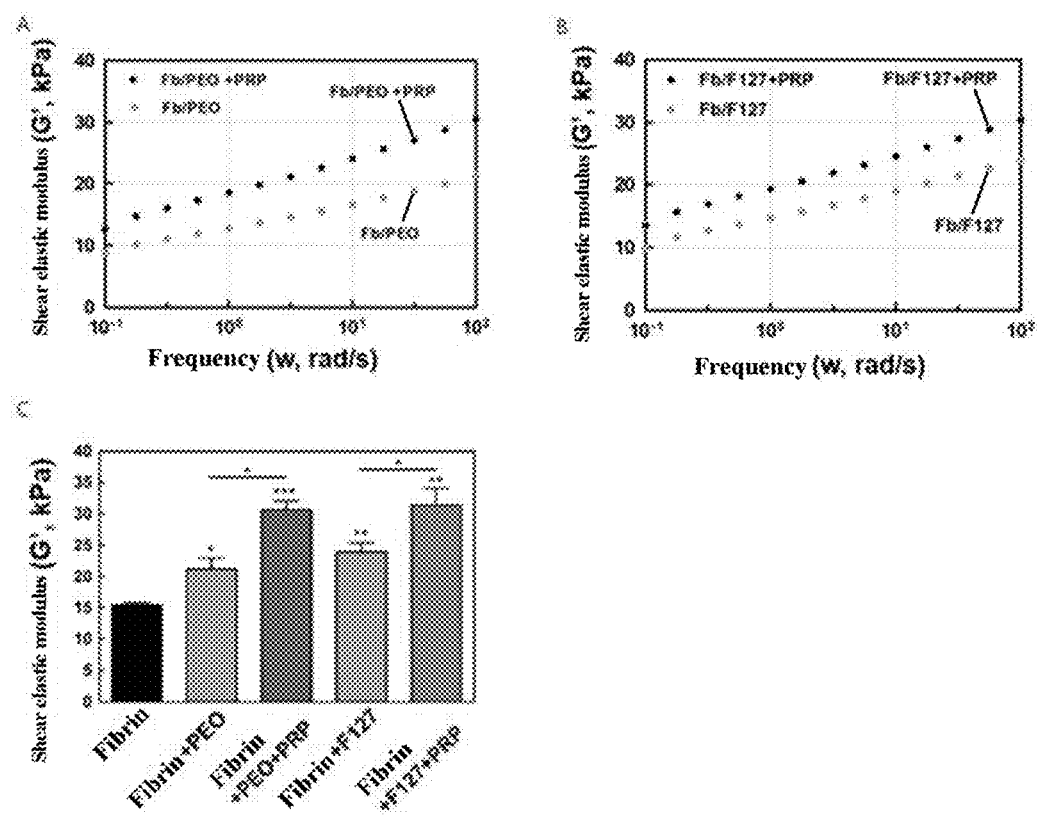

<FIG 5>
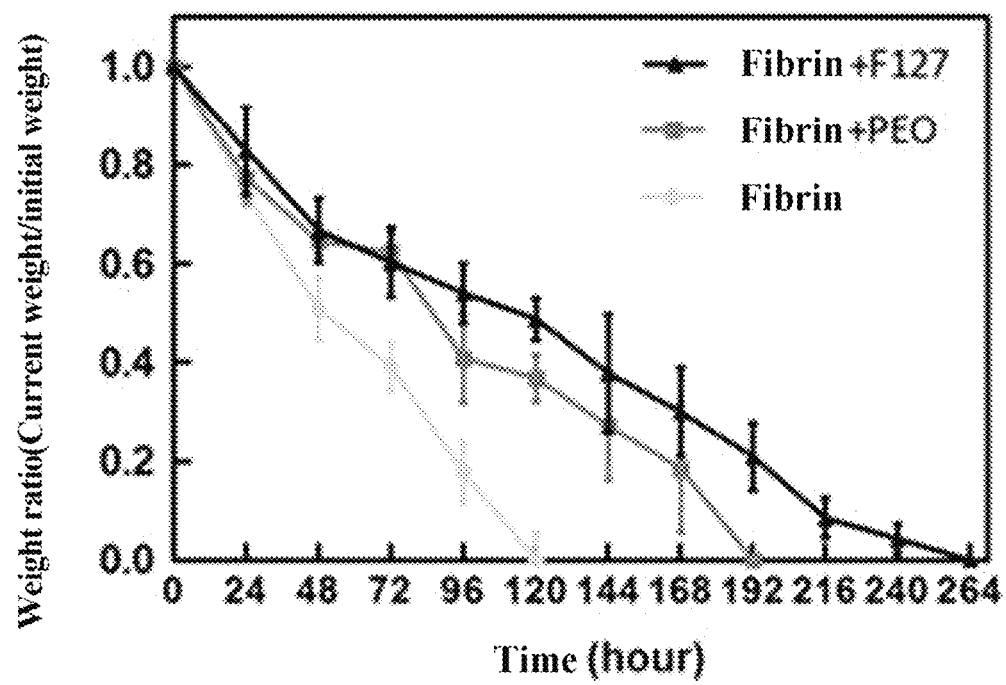

<FIG 6>
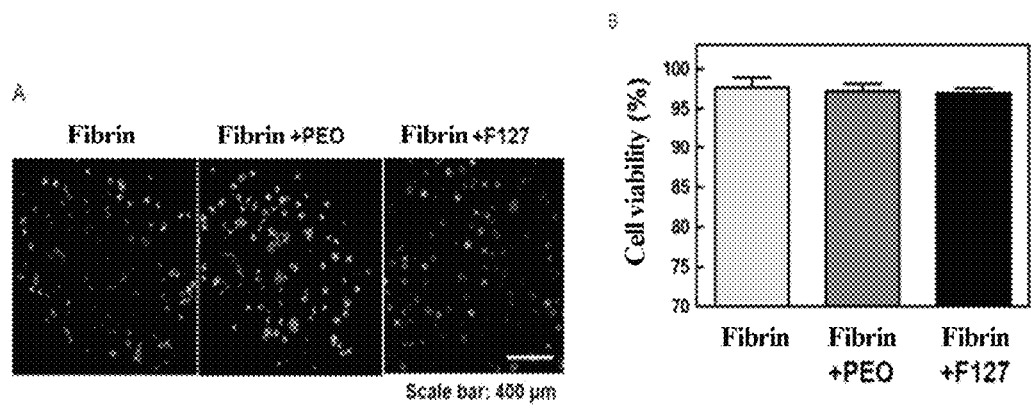

<FIG 7>
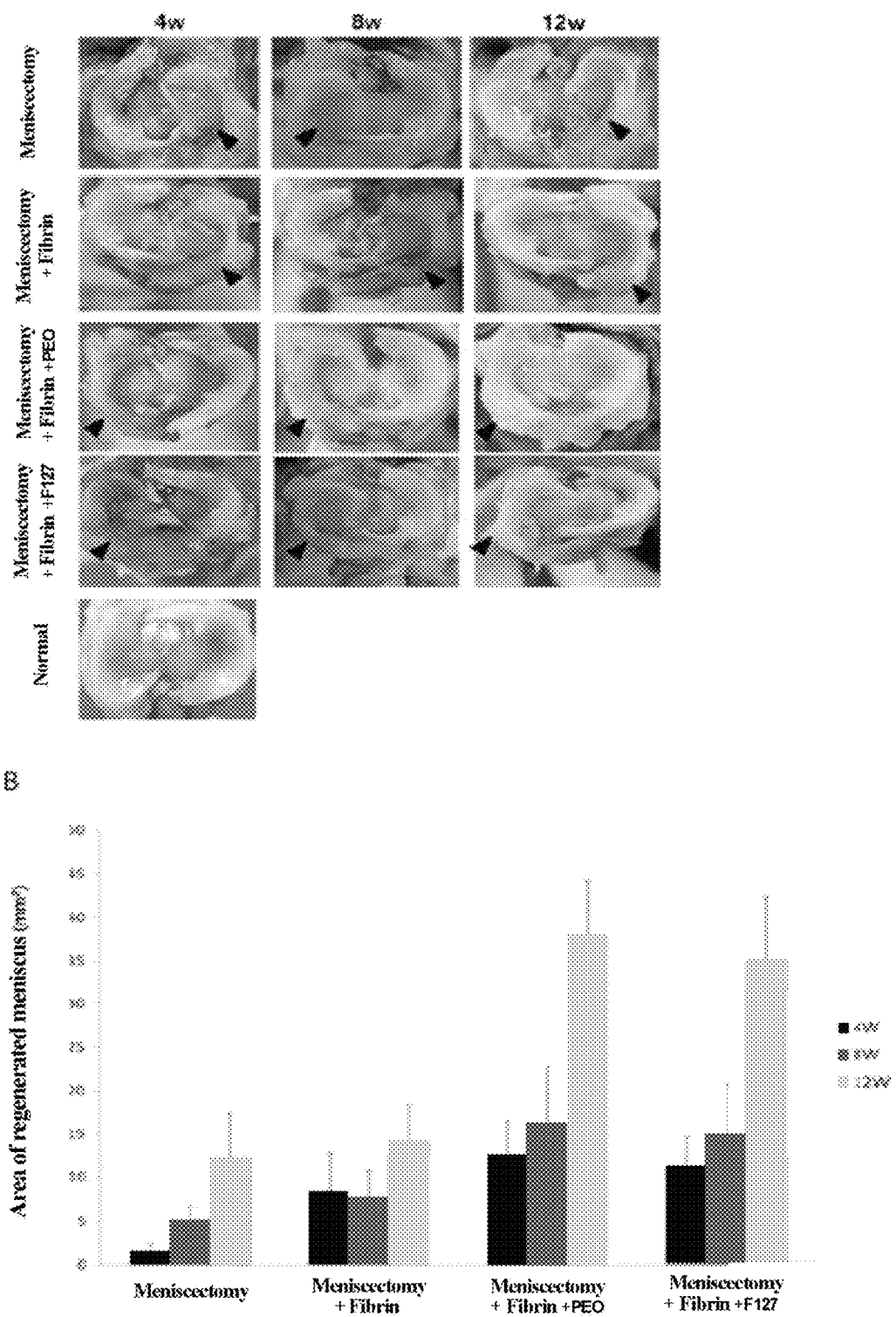

<FIG 8>
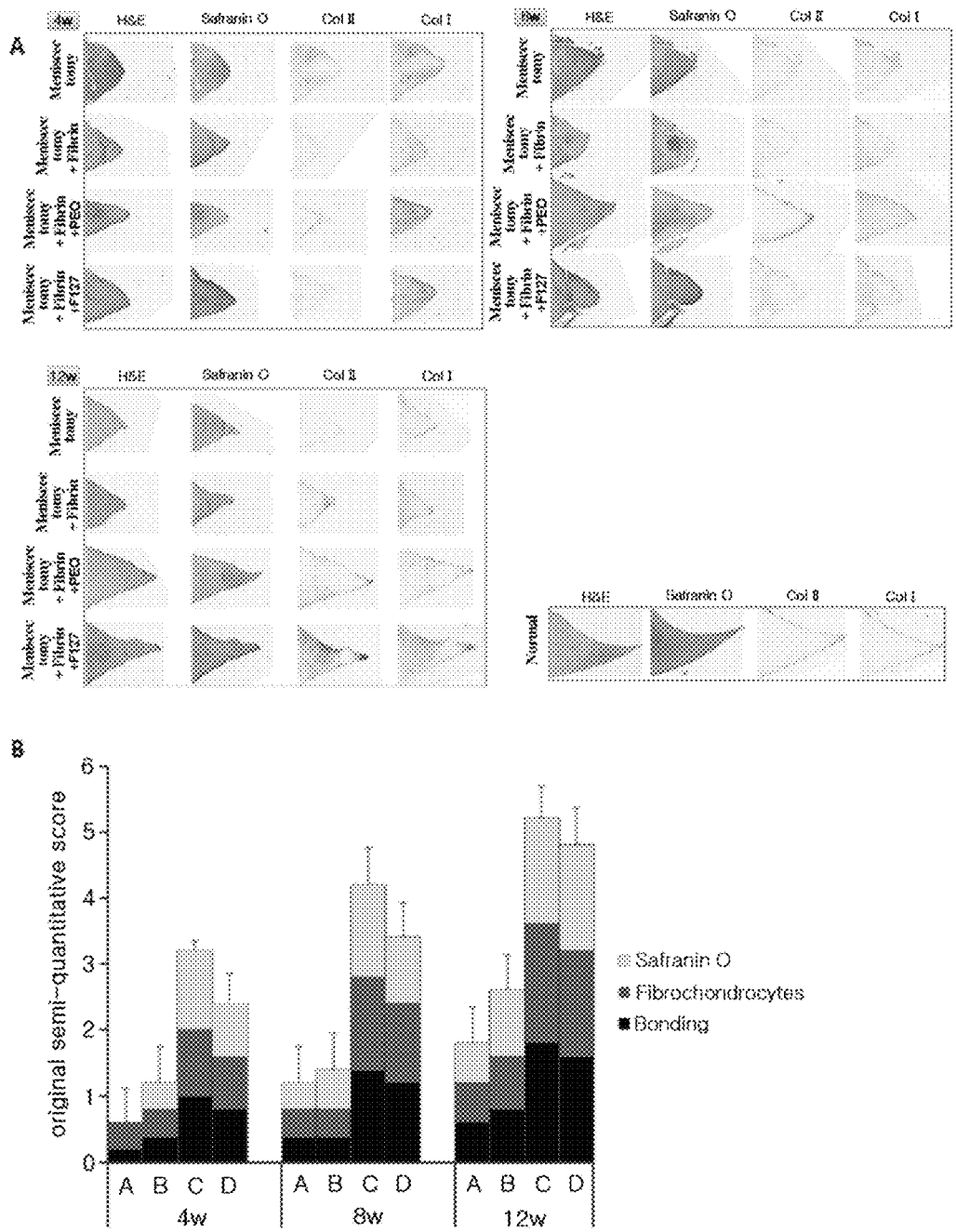

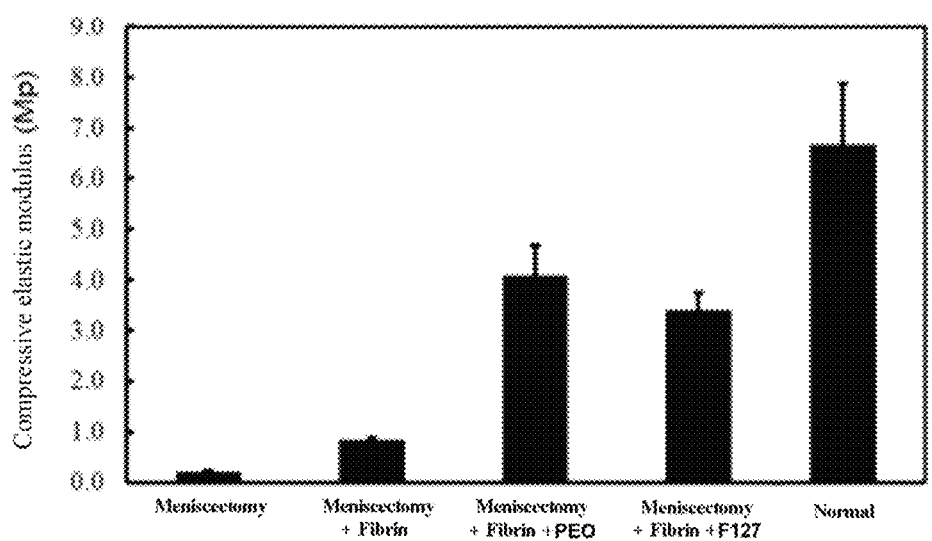
<FIG 9>

COMPOSITION FOR REGENERATION OF HUMAN FIBROUS CARTILAGE OR ELASTIC CARTILAGE

RELATED APPLICATIONS

This application is a 35 U.S.C. § 371 national phase application of PCT Application PCT/KR2018/016892 filed Dec. 28, 2018, which claims priority to Korean Application No. 10-2017-0183688 filed Dec. 29, 2017. The entire contents of each are incorporated herein by reference in its entirety.

FIELD OF THE INVENTION

The present disclosure relates to a composition and a kit for regeneration and treatment of fibrous cartilage or elastic cartilage, and a method for regeneration of fibrous cartilage or elastic cartilage using the same.

BACKGROUND OF THE INVENTION

Cartilage is composed of connective tissue cells and extracellular matrix like other connective tissues. However, the cartilage is a special connective tissue that contains a rigid yet somewhat flexible matrix unlike native connective tissues. The cartilage is classified into hyaline cartilage, elastic cartilage, and fibrous cartilage depending on types and characteristics of fibers constituting a cartilage matrix. Hyaline cartilage mainly contains type II collagen, and is the most common type of cartilage. The type II collagen is observed mainly in a form of microfibrils. A fiber component and a ground substance thereof are observed to be homogeneous because the microfibrils have substantially the same refractory index as that of glycoprotein as a main component of the ground substance. Elastic cartilage is distinguished from hyaline cartilage in that elastic fibers are rich in a matrix of the elastic cartilage. The fibrous cartilage has a ground substance in a smaller amount than other cartilages have. The fibrous cartilage has a large amount of collagen fibers, and most of these fibers are arranged in a uniform direction. The collagen fibers that constitute the fibrous cartilage has a type I collagen. Hyaline cartilage is observed in an articular surface, a costal cartilage, trachea, and bronchus laryngeal cartilage. The elastic cartilage constitutes an external ear and epiglottis and a portion of laryngeal cartilage. Fibrous cartilage is present in an intervertebral disc, symphysis pubis, intra-articular meniscus, and intra-articular fibrocartilage complex.

Meniscus belonging to the fibrous cartilage is located between femoral and tibial articular surfaces and is one of structures that play a very important role in maintaining a function of a knee joint. The meniscus disperses a load a and stress of the knee joint and absorbs shock, and lubricates a joint cartilage, and plays a very important role in protecting the joint cartilage by absorbing external shocks. The meniscus is formed of a half moon-shaped cartilage located in a middle of the knee joint. The meniscus acts as a shock absorber between joints, and thus absorbs a shock so that the joint cartilage is not damaged when a person is standing, walking or running such that a weight is transferred vertically downwardly.

Specifically, the meniscus has two crescent-shaped cartilages in each of the left and right knee joints. The two crescent-shaped cartilages are referred to as a lateral collateral meniscus and a medial collateral meniscus, respectively. An anterior cruciate ligament and a posterior cruciate ligament extend between the lateral collateral meniscus and the medial collateral meniscus, thereby to connect an upper thigh bone and a lower shin bone to each other.

The meniscus of athletes is often damaged. This is called 'meniscus tear.' The meniscus tear usually occur during exercise. However, when a middle aged people in late 50s to mid 60s have degenerative arthritis, a back of the meniscus is suddenly cut off, causing the meniscus tear. When middle-aged women do housework, they squat or bend their knees for a long time, thereby often causing the meniscus area tear. Thus, when the meniscus is torn or damaged, drug administration or surgical treatment will be performed. A collagen component of an extracellular matrix helps to enhance meniscus strength. Proteoglycan ECM component contributes to shock absorption. Further, a crescent-shaped tissue contains a vascularized outer part and an inner avascular area. When the tissue damage is in the outer part in which blood vessels are present, a suture surgery may be performed. However, this is not always the case. When the tissue damage is in an avascular region without blood vessels, natural healing is not possible, so that an ablation procedure is performed. Current surgical treatments may be classified into partial meniscectomy and subtotal or total meniscectomy depending on a size or a location of the meniscus tissue damage. The removal of the tissues by the meniscectomy ultimately leads to degenerative arthritis. Thus, medical technology for regeneration of damaged meniscus as a fundamental treatment method is required.

A current treatment method to prevent the occurrence of degenerative arthritis due to meniscus deficiency includes "allograft meniscal transplantation" and "meniscus regeneration treatment using synthetic substitute." The allograft meniscal transplantation requires a donor implant that has the same size and shape as a target meniscus. Clinical results of the allograft meniscal transplantation are still poor due to problems such as removal of a non-damaged meniscus portion and fixation of the implant.

Medical device development for meniscus regeneration is currently in an initial stage worldwide. Medical devices such as Actifit (Orteq Ltd.) and NUsurface (Active Implants LLS) using polyurethane, and Menaflex (ReGen Biologics, Inc.) using collagen as a main component are currently developed. The products have been licensed for use in their own country. Clinical trials and FDA thereof have not been conducted in other countries. The products are in a very early stage because a current time is within 2 years from the clinical application date. The major drawback thereof includes matching a size or a shape between a target meniscus and a substitute, and fixing the substitute using a suture device.

A support-based transplantation scheme refers to a method of suturing the polymer support formed into an appropriate shape with a partially excised meniscus. Although this support-based transplantation scheme is evaluated as a scheme to replace the allograft meniscal transplantation, stability and effectiveness thereof have not been verified. Further, the support-based transplantation requires a specific shape of the support to be inserted into a meniscus position, such that an incision of the knee joint is essential.

Thus, there is a need for a technique in which there is no need to remove an entire meniscus unnecessarily as in the allograft meniscal transplantation, a donor meniscus is not required, matching of a size or a shape between a target meniscus and a substitute as in the current treatment of meniscus regeneration using the substitute is not required, and fixing the substitute using a suture device is not required and the meniscus is excellently regenerated.

DISCLOSURE

Technical Problem

The present inventors have studied a simpler and minimally invasive knee meniscus regeneration method by which the problems of the prior art in which the incision of the knee joint and the insertion of the substitute are required are solved. Thus, we have identified that when hydrogel produced using fibrinogen, thrombin, and physiologically-active polymer was used, the meniscus as the fibrous cartilage was effectively regenerated even in a minimally invasive manner Thus, the present disclosure has been completed. Therefore, a purpose of the present disclosure is to provide a composition and a kit for regeneration of fibrous cartilage or elastic cartilage, the composition or the kit containing the hydrogel produced using fibrinogen, thrombin and physiologically-active polymer.

Technical Solution

The present disclosure provides a composition for regeneration of fibrous cartilage or elastic cartilage, the composition containing hydrogel including: fibrin; and a physiologically-active polymer, wherein the physiologically-active polymer and the fibrin form an interpenetrating polymer network (IPN) structure.

Further, the present disclosure provides a scaffold for regeneration of elastic cartilage or fibrous cartilage, the scaffold containing the composition for regeneration of the cartilage.

Further, the present disclosure provides a kit for regeneration of fibrous cartilage or elastic cartilage, the kit including a first compartment containing a fibrinogen solution; and a second compartment containing thrombin and a physiologically-active polymer.

Further, the present disclosure provides a production method of a composition for regeneration of fibrous cartilage or elastic cartilage, the method including 1) preparing fibrinogen 10 to 1000 mg/ml as a first solution; and 2) mixing thrombin and physiologically-active polymer with each other to prepare a second solution.

Further, the present disclosure provides a method for regeneration of fibrous cartilage or elastic cartilage, the method including administering a composition for regeneration of fibrous cartilage or elastic cartilage according to the present disclosure to an individual in need of treatment.

Further, the present disclosure provides a pharmaceutical composition for prevention or treatment of fibrous cartilage or elastic cartilage defect disease, the composition containing hydrogel including: fibrin; and a physiologically-active polymer, wherein the physiologically-active polymer and the fibrin form an interpenetrating polymer network (IPN) structure.

Further, the present disclosure provides a method for treating fibrous cartilage or elastic cartilage defect disease, the method including administering a composition for regeneration of the fibrous cartilage or elastic cartilage according to the present disclosure to an individual in need of treatment.

Advantageous Effects

The composition and the kit for regeneration of cartilage according to the present disclosure may be easily injected into a portion of fibrous cartilage or elastic cartilage that should be regenerated or restored from injury in a minimally invasive way. The composition and the kit for regeneration of cartilage according to the present disclosure may exhibit resistance to degrading enzyme without toxicity in a body, and thus remains adhered to or stays attached to the damaged portion, thereby improving behavior of surrounding cells, thereby to induce effective regeneration of defect tissues of fibrous cartilage such as meniscus or elastic cartilage. Therefore, the composition according to the present disclosure may be usefully used in a field of bio-biomaterials as a medium to help regeneration of a defect region of a biological tissue.

DESCRIPTION OF DRAWINGS

FIG. 1 is a schematic diagram of a composition and a kit for regeneration of fibrous cartilage or elastic cartilage according to the present disclosure, and a diagram showing hydrogel produced therefor. Panel A shows a syringe-type kit containing a mixture of fibrinogen and thrombin and polyethylene oxide (PEO) or PLURONIC® (F127), and shows hydrogel according to the present disclosure as produced using fibrin and physiologically-active polymer, wherein fibrin and physiologically-active polymer form an interpenetrating polymer network (IPN) structure.

Panel B shows a syringe-type kit containing a mixture of fibrinogen, platelet-rich plasma (PRP) and thrombin and polyethylene oxide (PEO) or PLURONIC® (F127), and shows hydrogel according to the present disclosure as produced using fibrin and physiologically-active polymer, wherein fibrin and physiologically-active polymer form an interpenetrating polymer network (IPN) structure.

FIG. 2 is a diagram showing an elastic modulus of hydrogel according to change in thrombin concentration. Panel A is a diagram showing shear elastic modulus. Panel B is a diagram showing compressive elastic modulus (student t-test, *$p<0.05$, $p<0.01$, *$p<0.001$).

FIG. 3 is a diagram showing changes in compressive elastic modulus and shear elastic modulus of hydrogel according to concentration change of polyethylene oxide (PEO) and PLURONIC® 127 (F127) under thrombin concentration 1250 U/ml. Panel A is a diagram showing change of the compressive elastic modulus according to PEO concentration of hydrogel as produced using thrombin and PEO. Panel B is a diagram showing change in the compressive elastic modulus according to F127 concentration of hydrogel as produced using thrombin and F127. Panel C is a diagram showing change in the shear elastic modulus according to PEO concentration of the produced hydrogel (student t-test, *$p<0.05$, $p<0.01$, *$p<0.001$).

FIG. 4 is a diagram showing change in a shear elastic modulus based on PRP addition, under conditions of thrombin concentration 1250 U/ml, polyethylene oxide (PEO) 5.0%, and PLURONIC® 127 (F127) 10.0%. Panel A is a diagram showing a result of identifying a shear elastic modulus of each of fibrin-PEO hydrogel (Fb/PEO) and PRP-added hydrogel (Fb/PEO+PRP). Panel B is a diagram showing a result of identifying a shear elastic modulus of each of fibrin-F127 hydrogel (Fb/F127) and PRP-added hydrogel (Fb/F127+PRP). Panel C is a comparison graph between shear elastic moduli of fibrin, fibrin-PEO, fibrin-PEO-PRP, fibrin-F127, and fibrin-F127-PRP hydrogels (*, , * at a top of the graph show statistical significances when compared with a fibrin group).

FIG. 5 is a diagram showing a decomposition pattern of fibrin-F127, and fibrin-PEO hydrogels and an only fibrin treated group as a control in trypsin enzyme treatment.

FIG. 6 is a diagram showing cell viability after 24 hours of cells mixed with a produced hydrogel. Panel A is a diagram showing a result observed with a fluorescent microscope. Panel B is a graph showing cell viability.

FIG. 7 is a diagram showing a result of regeneration of a meniscus damaged portion of rabbit. Panel A is a visual result showing regeneration of meniscus observed at 4, 8, and 12 weeks after injection of fibrin, fibrin-PEO, and fibrin-F127 hydrogels to the rabbit one week after meniscus injury. Panel B is a graph showing a result of measuring an area of a regenerated meniscus.

FIG. 8 is a diagram showing a result of regeneration of a meniscus damaged portion of rabbit. Panel A shows results (×40) of Hematoxylin & Eosin (H & E), Safranin O staining, and immunostaining of Type I collagen, showing regeneration of meniscus observed at 4, 8, and 12 weeks after injection of fibrin-PEO, and fibrin-F127 hydrogels to the rabbit one week after meniscus injury. Panel B is a diagram showing a histological tissue quality score (A. meniscectomy, B. meniscectomy+only fibrin treated group, C. meniscectomy+fibrin+PEO, and D. meniscectomy+fibrin+F127).

FIG. 9 is a diagram showing a result of measuring a strength of meniscus due to regeneration of a meniscus damaged portion of rabbit.

MODES OF THE INVENTION

Hereinafter, the present disclosure will be described in detail.

The present disclosure provides a composition for regeneration of fibrous cartilage or elastic cartilage, the composition containing hydrogel including: fibrin; and a physiologically-active polymer, wherein the physiologically-active polymer and the fibrin form an interpenetrating polymer network (IPN) structure.

The hydrogel according to the present disclosure may include the interpenetrating polymer network. The interpenetrating polymer network may be obtained when a polymer chain of the physiologically-active polymer randomly penetrates into a fibrin polymer network formed via action between fibrinogen and thrombin. The hydrogel having the interpenetrating polymer network structure does not exhibit cytotoxicity and thus has excellent biocompatibility, and may be injected into a portion of fibrous cartilage or elastic cartilage that should be regenerated even in a minimally invasive manner. Further, the hydrogel having the interpenetrating polymer network structure does not decompose for a long time in the injected portion, and may be adhered or attached to the damaged portion and may stay for a long time, thereby improving the behavior of surrounding cells, and, thus, to effectively induce regeneration of the fibrous cartilage or the elastic cartilage. Thus, the hydrogel having the interpenetrating polymer network structure may be effective for regeneration of fibrous cartilage and elastic cartilage, more preferably, meniscus regeneration.

In the present disclosure, the physiologically-active polymer may include, without limitation, a polymer capable of randomly penetrating the fibrin polymer network and thus forming an interpenetrating polymer network based hydrogel. Examples thereof may include at least one or more selected from the group consisting of alginate, chitosan, hyaluronic acid, polyethylene glycol (PEG), cellulose, poly (acrylic acid) (PAA), poly (glycolic acid) (PGA), poly (lactic acid) (PLA), PLA-PGA, PLA-PEG, dextran, dextran-PEG, starch, collagen base gel, agarose, PLURONIC® acid, heparan sulfate, glycosaminoglycan, polyethylene oxide (PEO), a copolymer of ethylene oxide and propylene oxide (P(EO-co-PO)), and a PLURONIC®/poloxamer. Preferably, the physiologically-active polymer may be at least one selected from the group consisting of polyethylene oxide (hereinafter, PEO) or PLURONIC® 127 (hereinafter, F127).

In the present disclosure, a regeneration target cartilage may include fibrous cartilage or elastic cartilage among hyaline cartilage, fibrous cartilage, or elastic cartilage. A fibrous cartilage is a cartilage in which white fibrous and cartilage tissues are mixed in various proportions and is resistant to compression, but is well torn and arranged in a dense state. The fibrous cartilage is in connection with the hyaline cartilage or connective tissue, and thus acts as a shock absorber in a portion where distortion or compression occurs to allow limited movement and acts to retain elasticity. The hyaline cartilage is mainly composed of type II collagen. Although the fiber component and ground substance are observed uniformly in the hyaline cartilage, elastic cartilage is different from hyaline cartilage in that elastic fibers are rich in the matrix of the elastic cartilage. Fibrous cartilage has a distinct difference from the hyaline cartilage and elastic cartilage in that the fibrous cartilage has less ground substance, and more collagen fibers, and the fibers are connected to each other in a regular arrangement. In particular, the collagen of collagen fibers constituting the fibrous cartilage is type I collagen. Unlike elastic cartilage and hyaline cartilage, the fibrous cartilage has no distinct cartilage membrane. It is known that bundles of I-type collagen fibers that form a layer in the fibrous cartilage are arranged at right angles to neighboring layers. Due to this characteristic arrangement of the fibrous cartilage, the fibrous cartilage may allow special elasticity in the discs between the vertebrae and withstand the pressure created by weight loads.

In the present disclosure, the fibrous cartilage or the elastic cartilage to be regenerated or recovered the injury includes various fibrous cartilage in the intervertebral disc or labrum acetabulare or articular meniscus, and the various elastic cartilage present in the external ear, epiglottis, and a laryngeal cartilage portion. The fibrous cartilage or the elastic cartilage to be regenerated or recovered the injury may be one or more selected from the group consisting of intervertebral disc cartilage, symphysis pubis cartilage, meniscus, intra-articular fibrocartilage complex, temporomandibular joint cartilage, discus articularis of the sternoclavicular joint, acetabular fossa cartilage, external ear, epiglottis, and laryngeal cartilage.

In the present disclosure, meniscus is located between femoral and tibial articular surfaces and is one of structures that play a very important role in maintaining a function of a knee joint. The meniscus disperses a load a and stress of the knee joint and absorbs shock, and lubricates a joint cartilage, and plays a very important role in protecting the joint cartilage by absorbing external shocks. The meniscus is formed of a half moon-shaped cartilage located in a middle of the knee joint. The meniscus acts as a shock absorber between joints, and thus absorbs a shock so that the joint cartilage is not damaged when a person is standing, walking or running such that a weight is transferred vertically downwardly. Therefore, the meniscus is known to be very important in the prevention of degenerative arthritis.

The hydrogel according to the present disclosure including: fibrin; and a physiologically-active polymer, wherein the physiologically-active polymer and the fibrin form an interpenetrating polymer network (IPN) structure has decomposition resistance to trypsin in vivo. Under the same conditions, the hydrogel according to the present disclosure has a decomposition resistance of 60 to 84 hours or more as compared to the decomposition time of fibrin, and thus is maintained in a gel form for a longer time. Thus, the hydrogel according to the present disclosure may remain in the target portion for a long time in the body to induce fibrous cartilage regeneration more effectively.

The hydrogel according to the present disclosure may exhibit a shear elastic modulus of 15 to 40 kPa under 100 radian/sec frequency conditions and may represent a compressive elastic modulus of 10 to 200 kPa. Since the hydrogel according to the present disclosure exhibits the elastic modulus as described above, the hydrogel may maintain flexibility and elasticity without being hard during fibrous cartilage regeneration. Thus, regardless of the size and shape of the fibrous cartilage defect portion, the hydrogel according to the present disclosure may be easily administered thereto. When surrounding cells are introduced into the administered hydrogel, the tissue regeneration may be achieved.

The composition according to the present disclosure may further contain platelet-rich plasma (PRP). The platelet-rich plasma may be provided in the form of a mixture with fibrinogen as a preparation material for the hydrogel. When the platelet-rich plasma is further contained therein, the hydrogel may exhibit a better shear elastic modulus under 100 radian/sec frequency conditions.

The composition according to the present disclosure is in a form of a hydrogel composition for fibrous cartilage regeneration. A syringe or the like may be used to allow the composition to be effectively administered to a portion of fibrous cartilage or elastic cartilage to be subjected to minimally invasive regeneration. The composition according to the present disclosure may preferably be used for regeneration of fibrous cartilage or elastic cartilage, and may be used as a support for regeneration of fibrous cartilage or elastic cartilage.

Therefore, the present disclosure provides a scaffold for regeneration of fibrous cartilage or elastic cartilage, the scaffold containing the composition for regeneration of fibrous cartilage or elastic cartilage according to the present disclosure.

Further, the present disclosure provides a kit for regeneration of fibrous cartilage or elastic cartilage, the kit including a first compartment containing a fibrinogen solution; and a second compartment containing thrombin and a physiologically-active polymer.

The kit according to the present disclosure includes two or more compartments which contain the fibrinogen solution and thrombin and physiologically-active polymer in the divided manner. For example, preferably, the kit according to the present disclosure includes compartments which contain materials for producing the fibrin-PEO or fibrin-F217 hydrogel in a divided manner. The first solution in the first compartment and the second solution in the second compartment may be mixed with each other in a double syringe. Immediately, the fibrin formation and the interpenetrating polymer network structure formation may occur to form a three-dimensional hydrogel.

The first compartment may further contain platelet-rich plasma in addition to fibrinogen. When the hydrogel further contains the platelet-rich plasma, better shear elastic modulus may be exhibited. The fibrinogen and the platelet-rich plasma may be mixed in a volume ratio of 1:0.1 to 1:1, preferably 1:0.1 to 1:0.8 and then the mixture may be contained in the first compartment.

The kit according to the present disclosure is configured to contain a first solution and a second solution for in first and second compartments respectively, wherein the first solution and the second solution are the materials for producing the hydrogel including: fibrin; and a physiologically-active polymer, wherein the physiologically-active polymer and the fibrin form an interpenetrating polymer network (IPN) structure. The first compartment may contain fibrinogen as the first solution at a concentration of 10 to 1000 mg/ml, preferably at a concentration of 10 to 500 mg/ml, more preferably at a concentration of 50 to 200 mg/ml. In the first compartment, antifibrinolytic agent may be further contained in the first solution. For example, aprotinin may be additionally contained therein preferably at 0.5 mg/ml (3 to 8 TIU/mg). In terms of a KTU unit, the aprotinin may be contained at a concentration of 100 to 5500 KIU/ml, preferably 1950 to 5200 KIU/ml. The second compartment may contain the second solution. The second solution may contain thrombin and physiologically-active polymer. The thrombin may be contained at 100 to 5000 Unit (U)/ml in the second solution and may be preferably contained at a concentration of 250 U/ml to 3000 U/ml, more preferably at a concentration of 250 to 2800 U/ml therein. The thrombin may have a final concentration of 250 U/ml to 1250 U/ml in the final mixed composition. Calcium chloride ($CaCl_2$) may be contained at 5 to 50 mg/ml, therein. Preferably, calcium chloride ($CaCl_2$) may be additionally contained therein at 5 (w/v) %. The physiologically-active polymer may contain, without limitation, a polymer capable of randomly penetrating the fibrin polymer network and thus forming an interpenetrating polymer network based hydrogel. Examples thereof may include at least one or more selected from the group consisting of alginate, chitosan, hyaluronic acid, polyethylene glycol (PEG), cellulose, poly (acrylic acid) (PAA), poly (glycolic acid) (PGA), poly (lactic acid) (PLA), PLA-PGA, PLA-PEG, dextran, dextran-PEG, starch, collagen base gel, agarose, PLURONIC® acid, heparan sulfate, glycosaminoglycan, polyethylene oxide (PEO), a copolymer of ethylene oxide and propylene oxide (P(EO-co-PO)), and a PLURONIC®/poloxamer. Preferably, the physiologically-active polymer may be at least one selected from the group consisting of PEO or F127. When the physiologically-active polymer is PEO, the PEO may be contained in 2 to 20% (w/v), preferably in 2 to 10 (w/v) % in the second solution such that the concentration of PEO in the final mixed composition is 1 to 10% (w/v), preferably 1 to 5% (w/v). Further, when the physiologically-active polymer is F127, F127 may be contained in the second solution at 2 to 40 (w/v) %, preferably 6 to 20 (w/v) % so that the concentration of F127 in the final mixed composition is 1 to 20 (w/v) %, preferably 3 to 10 (w/v) %.

In the present disclosure, the kit may be used interchangeably with a medical device used for medical purposes, and a preferred form thereof may be a double syringe form.

Further, the present disclosure provides a production method of a composition for regeneration of fibrous cartilage or elastic cartilage, the method including 1) preparing fibrinogen 10 to 1000 mg/ml as a first solution; and 2) mixing thrombin and physiologically-active polymer with each other to prepare a second solution.

The production method according to the present disclosure may include the production step of the preparation material for producing the hydrogel for regeneration of fibrous cartilage or elastic cartilage. Thus, when treatment/procedure is required for an individual requiring fibrous cartilage or elastic cartilage regeneration, the hydrogel may be rapidly produced and then the hydrogel may be injected into a joint cavity in a minimally invasive manner. That is, the production method according to the present disclosure includes a preparation process of the first solution containing fibrinogen as the main component, and a preparation process of the second solution having the mixture of thrombin and physiologically-active polymer, preferably PEO or F127 as the main component, and a process of mixing the first solution and the second solution in the double syringe and solidifying the mixed solution to form the hydrogel which may be injected into the body.

Therefore, the present disclosure further includes: 3) mixing the first solution and the second solution with each other to form a hydrogel for regeneration of fibrous cartilage or elastic cartilage in which the fibrin and the physiologically-active polymer form an interpenetrating polymer network (IPN) structure.

Further, in the production method according to the present disclosure, the first solution may further contain the platelet-rich plasma. The method may further include mixing the fibrinogen and the platelet-rich plasma in a volume ratio of 1:1 to 1:2.

The first solution or the second solution according to the present disclosure may further contain physiologically active substances required for fibrous cartilage or elastic cartilage regeneration. The physiologically active substances may be a cell culture medium or a growth factor.

Further, the present disclosure provides a method for regeneration of fibrous cartilage or elastic cartilage, the method including administering a composition for regeneration of fibrous cartilage or elastic cartilage according to the present disclosure to an individual in need of treatment.

Further, the present disclosure provides a pharmaceutical composition for prevention or treatment of fibrous cartilage or elastic cartilage defect disease, the composition containing hydrogel including: fibrin; and a physiologically-active polymer, wherein the physiologically-active polymer and the fibrin form an interpenetrating polymer network (IPN) structure.

Further, the present disclosure provides a method for treating fibrous cartilage or elastic cartilage defect disease, the method including administering a composition for regeneration of the fibrous cartilage elastic cartilage according to the present disclosure to an individual in need of treatment.

The step of administering the composition for regeneration of fibrous cartilage or elastic cartilage according to the present disclosure may include mixing the first solution and the second solution contained in the kit according to the present disclosure to immediately form the hydrogel including: fibrin; and a physiologically-active polymer, wherein the physiologically-active polymer and the fibrin form an interpenetrating polymer network (IPN) structure, and injecting the produced hydrogel into the joint cavity in a minimally invasive manner. The hydrogel exhibits degrading enzyme resistance in the injected portion for a long time and adheres to or stays attached to the damaged portion, thereby improving the behavior of surrounding cells to effectively achieve regeneration of fibrous cartilage or elastic cartilage, preferably damaged knee meniscus. The regenerated meniscus has excellent shear and compressive elasticity, and may maintain 50 to 80% strength of a normal meniscus. Thus, the produced hydrogel has superior strength compared to a commercially available fibrin-only hydrogel and is very effective in regeneration of fibrous cartilage or elastic cartilage and in treatment of fibrous cartilage or elastic cartilage defect diseases.

The fibrous cartilage or elastic cartilage defect refers to fibrous cartilage damage in which fibrous cartilage, fibrous cartilage tissue, and/or joint tissue (synovial membrane, articular capsule, subchondral bone, etc.) are injured by mechanical stimulation or an inflammatory reaction, or elastic cartilage damage or defect due to other congenital or acquired factors. The disease caused by the fibrous cartilage or elastic cartilage defect may preferably be a disease caused by the damage or defect of the fibrous cartilage or the elastic cartilage. More preferably, the disease caused by the fibrous cartilage or elastic cartilage defect may be one or more selected from the group consisting of lumbar herniated intervertebral disc, interpubic disc damage, temporomandibular joint damage, discus articularis damage of sternoclavicular joint, triangular fibrous cartilage complex tear of a wrist joint, ulnocarpal impaction syndrome, degenerative arthritis, meniscus damage, rheumatoid arthritis, external ear defect, and epiglottis or laryngeal cartilage defect. The lumbar herniated intervertebral disc is called a disc and may occur between the intervertebral bodies or between the pubic bones. The degenerative arthritis and rheumatoid arthritis are diseases that may be caused or exacerbated by damage to fibrous cartilage or elastic cartilage, and may be treated or improved via regeneration of fibrous cartilage or elastic cartilage or recovery of damage to fibrous cartilage or elastic cartilage. In this regard, currently, minimal resection is performed during meniscus resection for the treatment of initial degenerative osteoarthritis of the knee joint, or surgical procedures such as meniscus transplantation are performed to minimize or replace the loss of fibrous cartilage or elastic cartilage when the meniscus defect is severe, thereby reduce the incidence of degenerative osteoarthritis.

The treatment method may include injecting or implanting the composition directly into a target portion, such as a joint. The administration of the composition may be performed on a daily, weekly, several times per week, bimonthly, several times per month, monthly basis, or be performed in a necessary frequency to provide relief of symptoms. For intra-articular use of the composition, depending on the size of the joint and the severity of the condition, the amount of the composition as administered may be adjusted. The subsequent administration to the joint may be done in an intermittent manner according to the time of recurrence of symptoms in the joint.

The specific dosage level for any particular patient may be appropriately adjusted according to various factors such as activity of a specific compound as employed, age, weight, overall health, gender, diet, time of administration route of administration, excretion rate, drug combination, and severity of a particular disease being treated. The pharmaceutical composition may be produced and administered in a dosage unit. However, in special circumstances, a higher or lower dosage unit may be appropriate. Administration in the dosage unit may include single administration of the composition and/or multiple administrations of divided doses at specific intervals. Alternatively, the administration may be performed in several smaller sub dose units.

In one implementation, the fibrous cartilage or elastic cartilage defect disease is meniscus injury. The composition is administered to a joint space, for example a knee.

For example, an individual with the knee meniscus injury may receive 1, 2, or 3 injections of about 2, 3, 4, 5, 6, 7, 8, 9, 10 ml or more per knee. For other types of joints, a volume as administered may be adjusted based on a size of the joint.

However, a specific dosage level for any particular patient may be adjusted depending on various factors including an activity of a specific compound as employed, age, weight, overall health, sex, diet, time of administration, route of administration, excretion rate, drug combination and severity of the particular disease being treated.

The composition according to the present disclosure may additionally contain a pharmaceutically acceptable carrier in addition to the composition for regeneration of the fibrous cartilage or the elastic cartilage contained as an active ingredient.

The pharmaceutically acceptable carrier contained in the composition according to the present disclosure may include those as commonly used in formulation, including lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate and mineral oil, but being not limited thereto. The composition according to the present disclosure may additionally contain, in addition to the above compositions, lubricants, wetting agents, sweeteners, flavoring agents, emulsifying agents, suspending agents, preservatives, etc.

The pharmaceutical composition according to the present disclosure may be formulated with a pharmaceutically acceptable carrier and/or excipient and thus may be produced in a unit dose form or may be incorporated into a multi-dose container, according to a method that may be easily carried out by those skilled in the art to which the present invention pertains. In this connection, the formulations may be in the form of solutions, suspensions or emulsions in oil or aqueous media, or in the form of ex-agents, powders, granules, tablets or capsules, and may further contain a dispersant or a stabilizer.

EXAMPLES

Example 1. Production of First Solution and Second Solution for Hydrogel Production In order to achieve the defected human tissue regeneration in only a minimally invasive manner, first and second solutions as materials for hydrogel production were produced.
1.1 Production of Hydrogel Production Materials Using Fibrin and Polyethylene Oxide (PEO)

The first solution and the second solution as materials for producing the hydrogel were produced using fibrin and PEO. The first solution was produced by mixing fibrinogen (Sigma-Aldrich) 10 to 1000 mg/ml and aprotinin (Sigma-Aldrich) 100 to 5500 KIU/ml. The second solution was produced by dissolving PEO and calcium chloride in a solvent in which thrombin (REYON Pharmaceutical Co., Ltd) powder was dissolved at a concentration of 100 to 2500 Unit (U)/mL, at 37° C. The concentration of PEO was 1 to 100 mg/ml, and the concentration of calcium chloride was 5 to 50 mg/ml. The hydrogel having the interpenetrating polymer network structure as produced by mixing the first solution and the second solution as thus produced was named 'fibrin-PEO.'
1.2. Production of Hydrogel Production Materials Using Fibrin and PLURONIC® 127 (F127)

The first solution and the second solution as materials for producing the hydrogel were produced using fibrin and F127. The first solution was produced in the same manner as specified in the Example 1.1. In the preparation of the second solution, F127 (Sigma Aldrich, P2443) was used at a concentration of 2 to 200 mg/ml and was dissolved in a thrombin solution in an ice bath at 0 to 4° C. The hydrogel having the interpenetrating polymer network structure produced by mixing the first solution and the second solution as thus produced was named 'fibrin-F127.'
1.3. Production of Hydrogel Production Material Using Fibrin and PEO Containing PRP The first solution contains fibrin and platelet-rich plasma (PRP) obtained from rabbit blood. The second solution contains PEO and thrombin. Thus, a fibrin-PEO hydrogel production material containing the PRP was produced. The first solution was produced by mixing fibrinogen solution and platelet-rich plasma in a volume ratio of 1.0:0.1 to 1.0:0.7. The second solution was produced in the same manner as in the Example 1.1. The hydrogel having the interpenetrating polymer network structure produced by mixing the first solution and the second solution as thus produced was named 'fibrin-PEO-PRP.'
1.4. Production of Hydrogel Production Materials Using Fibrin and F127 Containing PRP The first solution contains fibrin and platelet-rich plasma (PRP) obtained from rabbit blood. The second solution contains PLURONIC® 127 and thrombin. The interpenetrating polymer network containing was produced. The first solution was produced by mixing fibrinogen solution and platelet-rich plasma in a volume ratio of 1.0:0.1 to 1.0:0.7. The second solution was produced in the same manner as in the Example 1.2. The hydrogel having the interpenetrating polymer network structure produced by mixing the first solution and the second solution as thus produced was named 'fibrin-F127-PRP.'
1.5 Instant Gelation Identification In the produced Examples 1.1 to 1.4, the first solution and the second solution were contained in first and second compartments of the double syringe, respectively. During a procedure, each of the first and second solutions flowed out of the individual compartment and then the two solutions merged to produce an instant gelation to form a three-dimensional structure. The schematic diagram thereof and the solidified hydrogel are shown in FIG. 1.

As shown in FIG. 1, it was identified that all the hydrogel production materials of the Examples 1.1 to 1.4 of the present disclosure formed the three-dimensional structure hydrogel via the immediate gelation. The hydrogel produced in this way is characterized in that PEO or F127 partially penetrates between fibrins to form the IPN (interpenetrating polymer network).

Example 2. Identification of Compressive Elastic Modulus and Shear Elastic Modulus of Hydrogel According to Thrombin Concentration In order to identify the elastic modulus change of the hydrogel as produced according to combinations of concentrations of fibrinogen and thrombin, the shear elastic modulus and compressive elastic modulus were measured using a hydrogel formed in a mold having a diameter of 8.0 mm. The shear elastic modulus was measured using a rheometer (ARES-LS, TA Instruments), and a plate spacing was set to 900 μm, and a frequency condition was adjusted to a range from 0.1 to 100 Hz. The compressive elastic modulus was measured using a universal tensile tester (Instron 5966, Instron Corporation). In a stress-strain graph, the compressive elastic modulus (E) value was derived using a slope of a section with an elastic section. The concentration of the fibrinogen was fixed at a constant concentration of 100 mg/ml, while the thrombin concentration of the second solution was set to 500, 1000, 2500 U/mL before mixing so that the final concentration of thrombin after the mixing is 250 U/mL, 500 U/mL and 1250 U/mL. Thus, the hydrogel was produced via mixing therebetween. After the production thereof, the shear elastic modulus and the compressive elastic modulus of the hydrogel were measured and the results are shown in FIG. 2.

As shown in FIG. 2, from a result of identifying the change graph of the shear elastic modulus (A) and the compressive elastic modulus (B) of a simple polymer network hydrogel composed of the fibrinogen and the thrombin, based on the change in the thrombin concentration, it was identified that, when the thrombin concentration increased in an order of 250, 500, and 1250 U/ml, the shear elastic modulus of the fibrin hydrogel increased in an order of 14.1±1.0, 14.7±0.7, and 15.4±0.6 kPa at 100 rad/s, respectively. Further, it was identified that when the thrombin concentration increases in the order of 250, 500, and 1250 U/ml, the compressive elastic modulus of the fibrin hydrogel increases in the order of 29.9±3.1, 43.1±5.2, 93.6±9.0 kPa, respectively.

Example 3. Identification of Compressive Elastic Modulus in Addition of PEO and F127

The compressive elastic modulus of the hydrogel when PEO or F127 was added as the second solution was measured. The fibrinogen concentration in the first solution was fixed at a constant concentration of 100 mg/ml. The concentration of thrombin in the second solution was fixed at 2500 U/mL so that the concentration of thrombin in the final mixed composition was 1250 U/ml. The concentration of PEO in the second solution was changed to 2.0, 6.0, and 10.0% (w/v) so that the concentration of PEO in the final mixed composition was 1.0, 3.0, and 5.0% (w/v). The concentration of F127 was changed to 6.0, 14.0, and 20.0% (w/v) so that the F127 concentration in the final mixed composition was 3.0, 7.0, and 10.0% (w/v). Thu, the second solution was produced. The compressive elastic modulus change in each production example was identified and the results are shown in FIG. 3.

As shown in FIG. 3, when the hydrogel was prepared while the PEO concentration was set to 1.0, 3.0, and 5.0% (w/v), the compressive elastic modulus (A) thereof was 103.3±4.9 kPa, 108.4±4.8 kPa, 120.1±3.3 kPa, respectively. When hydrogel was prepared while the concentration of F127 was set to 3.0, 7.0, and 10.0% (w/v), the compressive elastic modulus (B) of the hydrogel was 72.0±4.3 kPa, 122.0±9.6 kPa, and 156.0±9.8 kPa, respectively.

Further, from a result of identifying the shear elastic modulus change of the fibrin-PEO hydrogel formed under varying PEO concentrations under the thrombin concentration 1250 U/ml, it was identified that when the PEO concentration was increased in an order of 1.0, 3.0, and 5.0%, the shear elastic modulus of the produced fibrin-PEO increased in an order of 15.4±1.3, 18.5±1.2, and 21.5±1.5 kPa at 100 rad/s, respectively.

Example 4. Identification of Compressive Elastic Modulus when Adding PRP to PEO and F127

The second solution was produced by mixing thrombin 2500 U/mL, and PEO 10.0% or F127 20.0%. The first solution was fibrinogen 200 mg/ml. The platelet rich plasma (PRP) was mixed with the first solution in a 1:1 volume ratio to produce a final fibrinogen concentration of 100 mg/ml. The first solution was mixed with the second solution to produce a hydrogel via immediate solidification. The hydrogel produced was named fibrin-PEO-PRP or fibrin-F127-RPR. In order to identify the effect of the platelet-rich plasma on the properties of the hydrogel, changes in the shear elastic modulus of the experimental group containing no platelet-rich plasma (fibrin-PEO, fibrin-F127) and the experimental group containing the fibrin alone were checked. The results are shown in FIG. 4 and Table 1.

TABLE 1

| Shear elastic modulus (kPa) at 100 rad/s | |
|---|---|
| Fibrin + PEO | 21.2 ± 2.98 |
| Fibrin + PEO + PRP | 30.59 ± 2.39 |
| Fibrin + F127 | 23.88 ± 2.55 |
| Fibrin + F127 + PRP | 31.32 ± 4.65 |

As shown in FIG. 4 and Table 1, from the result of measuring the shear elastic modulus, it was identified that, under the same conditions, both groups in which the fibrin is mixed with PEO and F127 respectively showed higher shear elastic modulus, when the platelet-rich plasma was added thereto.

Example 5. Comparison of Enzyme Decomposition Patterns for Identification of Sustained Effects in Body In order to identify the degradation in vitro under the enzymatic treatment of the hydrogel as produced by mixing the first solution and the second solution according to the present disclosure, the hydrogel was soaked in a 0.00125% trypsin solution and then a weight thereof was measured over time, and a decomposition rate was measured based on comparisons thereof with an initial weight. Specifically, in order to predict the fibrin decomposition pattern when injecting the fibrin-based hydrogel into the body, the decomposition pattern was identified in vitro using a representative fibrin proteolytic enzyme trypsin. FIG. 5 shows the results of identifying the decomposition pattern of the fibrin hydrogel as the control and the hydrogels formed using fibrin+PEO, fibrin+PEO+PRP, fibrin+F127, and fibrin+F127+PRP in the above Example 4 under the condition of 0.00125% trypsin/EDTA.

As shown in FIG. 5, the fibrin hydrogel as the control was completely degraded at 120 hours from the trypsin treatment start. However, among the hydrogels produced in the present disclosure, the fibrin+PEO group was degraded at 192 hours from the trypsin treatment start, and fibrin+F127 was degraded at 264 hours from the trypsin treatment start. That is, it was identified that the hydrogel produced in the present disclosure may delay the degradation by an average of 72 hours, due to the partial interpenetrating effect of PEO or F127 compared to the fibrin hydrogel as the control. Therefore, it was identified that the hydrogel according to the present disclosure may achieve the desired effect while staying in the body for a longer time.

Example 6. Biocompatibility Identification

A biocompatibility identification experiment was performed to identify whether the fibrin-PEO or fibrin-F127 hydrogel produced in the Example 4 is suitable for use as a therapeutic agent. Hydrogel was prepared by mixing fibrochondrocyte obtained from rabbit cartilage with the first solution containing fibrinogen at a concentration of $1 \times 10^5$ cells/mL and mixing the mixture with the second solution containing PEO or F127. Cells were encapsulated inside the hydrogel. Thereafter, the hydrogel was cultured in F-12 medium for 24 hours, and the live and dead cells were stained using Live/Dead assay kit (Invitrogen), respectively, and were observed using a fluorescence microscope (AMF4300, EVOS, Life Technology). Four 10-magnification images were taken, and the cell viability was calculated using a following formula and the calculated cell viabilities were compared with each other and the results are shown in FIG. 6.

Cell viability=(number of viable cells/number of total cells)×100

As shown in FIG. 6, when compared to the fibrin hydrogel as the control, the hydrogel produced by containing PEO or F127 was free of red stained dead cells. From a result of identifying the hydrogel cell survival/kill fluorescence images over time, it was found that there was no difference between the cell survival in the fibrin-PEO and fibrin-F127 hydrogels produced according to the present disclosure and the cell survival in the control fibrin hydrogel. Therefore, all of the hydrogels produced in accordance with the present disclosure were identified as having excellent biocompatibility even though they remained in the body for a long time when administered in vivo.

Example 7. Verification of Meniscus Regeneration Effects in Meniscus-Cartilage-Damaged Animal Model In order to verify whether the hydrogel produced using fibrin and PEO or fibrin and F127 as produced in the Example 4 exhibited a meniscus regeneration effect in a meniscus-damaged animal model, a following experiment was performed.

More specifically, in order to produce a rabbit joint cartilage-damaged animal model, a healthy rabbit was selected and then an appropriate amount of ketamine and rompun according to the weight were injected anesthesia thereto. It was identified that the rabbit was in a sufficiently general anesthesia state. After shaving the knee joint portions of both lower limbs, a bandage was fixed thereto while maintaining the posture. We disinfected both knee joints with povidone. After palpating the patella and identifying the position, an observation tool reached within the knee joint using a paramedian approach along the incision line passing through upper and lower portions of the knee and a portion inside the patella. The inside of the joint was observed while the knee joint was bent while the patella was moved outwardly. After identifying the absence of unusual pathological findings, meniscus was removed by two-thirds or more (meniscectomy), thus causing the meniscus damage. After the patella is returned to its original position, the soft tissue around the patella was closed with an absorbent thread. The skin was closed with a non-absorbent thread. After allowing the rabbit to wake up from anesthesia, the rabbit was allowed to move freely. Painkillers and antibiotics were administered thereto to prevent infection for 5 days after surgery. A week later, 100 mg/mL fibrinogen, and 0.5 mg/mL aprotinin were added in a compartment 1 of the prepared double syringe. Thrombin 2500 U/mL, calcium chloride 5 (w/v) % or thrombin 2500 U/mL, calcium chloride 5 (w/v) % and PEO 10.0%, or thrombin 2500 U/mL, calcium chloride 5 (w/v) % and F127 20.0% were added into a compartment 2. Without cutting the skin on the left side of the animal model, the above test substances were injected into the meniscus damaged portion. No substance was applied to an opposite leg. After 4 weeks, 8 weeks, and 16 weeks, the meniscus which had been damaged and then treated was removed from the rabbit and a visual evaluation thereof was performed. This was evaluated by measuring an area of the regenerated meniscus using an image program. Further, after fixing the tissue, H&E, Safranin O staining and immunostaining for Type I collagen were performed. The regenerated meniscus was analyzed via quantification using a histological tissue quality score. The results are shown in FIG. 7 and FIG. 8.

As shown in FIG. 7 and FIG. 8, it was identified that in the groups injected with fibrin-PEO and fibrin-F127 hydrogels, fibrous tissue began to be generated since 4 weeks, and tissues similar to meniscus began to be generated since 12 weeks, compared to the hydrogel as the control as produced by containing only fibrin alone. These results show that meniscus may be regenerated at 4, 8, and 12 weeks after injecting the fibrin-PEO and fibrin-F127 hydrogels to the rabbit without skin incision one week after the meniscus damage in the rabbit. Therefore, when using the fibrin-PEO and fibrin-F127 hydrogels, meniscus cells may be generated with excellent efficiency due to the behavior of surrounding cells around the damaged knee meniscus portion, such that meniscus damage may be effectively treated.

Example 8. Compressive Strength Test of Regenerated Meniscus

An important property of the meniscus cartilage support is compressive strength at which the meniscus cartilage support may withstand external forces. Therefore, in the Example 7, the meniscus regenerated for 12 weeks was cut into 2 samples using a 4 mm punch, and then the compressive strength thereof was measured with a tensile force gauge. A strength of the meniscus regenerated via injecting the fibrin-PEO and fibrin-F127 hydrogels according to the present disclosure was identified, and the results are shown in FIG. 9.

As shown in FIG. 9, it was identified that the compressive strength of the tissue regenerated via the injections of the fibrin-PEO and fibrin-F127 hydrogels was significantly increased, compared to the group treated with nothing (meniscectomy only) and the group treated with the fibrin alone. Specifically, in the meniscectomy only which was not treated with anything, the Mpa value of the compressive strength was 203.3±43.2, and the Mpa value of the compressive strength was 844.9±32.6 in the group injected with fibrin alone. The Mpa value of the compressive strength was 4086.7±542.1 in the fibrin+PEO hydrogel-injected group, the Mpa value of the compressive strength was 3406.8±312.1 in the fibrin+F127 hydrogel-injected group, and the Mpa value of the compressive strength was 6688.6±1012.5 in the normal meniscus. Therefore, it was identified that the strength of the meniscus regenerated via injecting the fibrin+PEO hydrogel and the fibrin+F127 hydrogel according to the present disclosure was equal to or greater than 60% of that of the normal meniscus.

The invention claimed is:

1. A method for regeneration of fibrous cartilage or elastic cartilage, the method comprising administering a composition including hydrogel consisting of: fibrin; and a polyethylene oxide (PEO) or poloxamer as physiologically-active polymer, wherein the physiologically-active polymer and the fibrin form an interpenetrating polymer network (IPN) structure, wherein the hydrogel has a trypsin decomposition resistance.

2. The method of claim 1, wherein the fibrous cartilage or the elastic cartilage is at least one selected from the group consisting of intervertebral disc cartilage, symphysis pubis cartilage, meniscus, intra-articular fibrocartilage complex, temporomandibular joint cartilage, discus articularis of sternoclavicular joint, acetabular fossa cartilage, external ear, epiglottis, and laryngeal cartilage.

3. The method of claim 1, wherein the hydrogel has a shear elastic modulus of 15 to 40 kPa or a compressive elastic modulus of 10 to 200 kPa under 100 radian/sec.

4. A method for regeneration of fibrous cartilage or elastic cartilage, the method comprising administering a composition including hydrogel comprising: fibrin; physiologically-active polymer, and platelet-rich plasma (PRP), wherein the physiologically-active polymer and the fibrin form an interpenetrating polymer network (IPN) structure, wherein the hydrogel has a trypsin decomposition resistance.

5. A method for treating fibrous cartilage or elastic cartilage defect disease, the method comprising administering a composition including hydrogel consisting of: fibrin; and a polyethylene oxide (PEO) or poloxamer as physiologically-active polymer, wherein the physiologically-active polymer and the fibrin form an interpenetrating polymer network (IPN) structure, wherein the hydrogel has a trypsin decomposition resistance.

6. The method of claim 5, wherein the fibrous cartilage or elastic cartilage defect disease is at least one selected from the group consisting of lumbar herniated intervertebral disc, interpubic disc damage, temporomandibular joint damage, discus articularis damage of sternoclavicular joint, triangular fibrous cartilage complex tear of a wrist joint, ulnocarpal impaction syndrome, degenerative arthritis, meniscus damage, rheumatoid arthritis, external ear defect, and epiglottis or laryngeal cartilage defect.

* * * * *